US010434337B2

(12) United States Patent
Hanada et al.

(10) Patent No.: US 10,434,337 B2
(45) Date of Patent: Oct. 8, 2019

(54) PARTICLE BEAM ADJUSTMENT DEVICE, PARTICLE BEAM ADJUSTMENT METHOD, AND PARTICLE BEAM THERAPEUTIC DEVICE

(71) Applicant: KABUSHIKI KAISHA TOSHIBA, Minato-ku (JP)

(72) Inventors: Shinji Hanada, Ebina (JP); Yasushi Iseki, Yokohama (JP); Satoshi Kimura, Kawasaki (JP); Katsushi Hanawa, Kita (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 25 days.

(21) Appl. No.: 15/532,860

(22) PCT Filed: Dec. 4, 2014

(86) PCT No.: PCT/JP2014/006068
§ 371 (c)(1),
(2) Date: Jun. 2, 2017

(87) PCT Pub. No.: WO2016/088155
PCT Pub. Date: Jun. 9, 2016

(65) Prior Publication Data
US 2017/0368371 A1 Dec. 28, 2017

(51) Int. Cl.
*A61N 5/10* (2006.01)
*G21K 5/04* (2006.01)
(Continued)

(52) U.S. Cl.
CPC ............. *A61N 5/1065* (2013.01); *A61N 5/10* (2013.01); *A61N 5/1043* (2013.01);
(Continued)

(58) Field of Classification Search
CPC .......... A61N 2005/1087; A61N 5/1065; A61N 5/1067; A61N 5/1048; A61N 5/10; G21K 5/04
See application file for complete search history.

(56) References Cited

U.S. PATENT DOCUMENTS 5,017,789 A * 5/1991 Young ................. A61N 5/1043
250/396 ML
7,838,855 B2 * 11/2010 Fujii .................... A61N 5/1048
250/491.1
(Continued)

FOREIGN PATENT DOCUMENTS

JP 2002-58750 A 2/2002
JP 2003-282300 A 10/2003
(Continued)

OTHER PUBLICATIONS

International Search Report dated Mar. 3, 2015 in PCT/JP2014/006068, filed Dec. 4, 2014.
(Continued)

*Primary Examiner* — Wyatt A Stoffa
(74) *Attorney, Agent, or Firm* — Oblon, McClelland, Maier & Neustadt, L.L.P.

(57) ABSTRACT

A particle beam adjustment device includes: a position monitor that detects a positional deviation of a particle beam transported from a beam transport section; an interlock device to interrupt irradiation of the particle beam when a positional deviation of the particle beam is detected by the position monitor; a pair of screen monitors that measure position and angle of an axis of the particle beam; a correction electromagnet that controls the axis of the particle beam by adjusting a magnetic field on a basis of a signal indicating the particle beam position and angle measured by the screen monitors; and a beam scanning electromagnet that irradiates an irradiation target with the particle beam. One of
(Continued)

the screen monitors is installed outside a treatment room, and the other screen monitor and the position monitor are installed inside the treatment room.

7 Claims, 4 Drawing Sheets

(51) Int. Cl.
  *G21K 1/093* (2006.01)
  *H05H 7/04* (2006.01)
  *H05H 7/00* (2006.01)

(52) U.S. Cl.
  CPC ......... *A61N 5/1048* (2013.01); *A61N 5/1067* (2013.01); *A61N 5/1075* (2013.01); *A61N 5/1077* (2013.01); *G21K 1/093* (2013.01); *G21K 5/04* (2013.01); *H05H 7/001* (2013.01); *H05H 7/04* (2013.01); *A61N 2005/1087* (2013.01); *A61N 2005/1094* (2013.01); *H05H 2007/002* (2013.01); *H05H 2007/048* (2013.01)

(56) References Cited

U.S. PATENT DOCUMENTS

| | | |
|---|---|---|
| 8,552,408 B2 | 10/2013 | Hanawa et al. |
| 9,327,140 B2 | 5/2016 | Honda et al. |
| 2003/0183779 A1 | 10/2003 | Norimine et al. |
| 2004/0232356 A1* | 11/2004 | Norimine ............. A61N 5/1048 250/492.3 |
| 2005/0231138 A1* | 10/2005 | Nakanishi ............. G21K 5/04 315/500 |
| 2005/0247890 A1* | 11/2005 | Norimine ............. A61N 5/1048 250/492.3 |
| 2006/0118736 A1* | 6/2006 | Moriyama ............. A61N 5/10 250/493.1 |
| 2006/0273264 A1* | 12/2006 | Nakayama ............. H05H 7/10 250/492.3 |
| 2007/0076851 A1* | 4/2007 | Pellegrino ............. A61N 5/10 378/157 |
| 2008/0067451 A1* | 3/2008 | Guertin ............. A61N 5/10 250/503.1 |
| 2009/0039256 A1* | 2/2009 | Fujii ............. A61N 5/1048 250/306 |
| 2009/0184263 A1* | 7/2009 | Moriyama ............. H05H 7/04 250/492.3 |
| 2011/0073778 A1* | 3/2011 | Natori ............. A61N 5/1043 250/492.3 |
| 2011/0108737 A1* | 5/2011 | Pu ............. A61N 5/10 250/398 |
| 2013/0231517 A1* | 9/2013 | Iwamoto ............. G01T 1/29 600/1 |
| 2013/0253845 A1* | 9/2013 | Iwata ............. A61B 5/48 702/19 |
| 2014/0061498 A1* | 3/2014 | Honda ............. A61N 5/1043 250/397 |
| 2014/0110596 A1* | 4/2014 | Chang ............. H01J 37/12 250/396 R |
| 2014/0203186 A1* | 7/2014 | Iwamoto ............. H05H 7/12 250/397 |
| 2015/0038764 A1* | 2/2015 | Sugahara ............. A61N 5/1079 600/1 |
| 2015/0238780 A1* | 8/2015 | Nishimura ............. A61N 5/1043 600/2 |
| 2015/0352372 A1* | 12/2015 | Takayanagi ............. A61N 5/10 600/1 |

FOREIGN PATENT DOCUMENTS

| | | |
|---|---|---|
| JP | 2009-347 A | 1/2009 |
| JP | 2010-220975 A | 10/2010 |
| JP | 2010-253240 A | 11/2010 |
| JP | 2011-161055 A | 8/2011 |
| JP | 2012-64403 A | 3/2012 |
| JP | 2012-205837 A | 10/2012 |
| WO | WO 2013/027263 A1 | 2/2013 |

OTHER PUBLICATIONS

"[Kengakusha-yo] Carbon Ion Radiotherapy HIMAC", National Institute of Radiological Sciences, May 8, 2014, Internet <URL: http://www.nirs.go.jp/publication/pamphlets/index.shtml>, (4 pp).
"Sekai Saikosoku 3 Jigen Scanning Shoshaho o Mochiita Chiryo o Kaishi-Nippon Hatsu no Jisedaigata Juryushisen Gan Chiryo, Aratana Tenkai e-", National Institute of Radiological Sciences, Jun. 22, 2011, Internet <URL:http://www.nirs.go.jp/informaiion/press/2011/06_22.shtml>, (3pp).
Hikaru Soda et al., "Development of Scanning Irradiation in Gunma University Heavy Ion Medical Center", Proceedings of the 11th Annual Meeting of Particle Accelerator Society of Japan, (with English Abstract and Partial English translation), Aug. 2014, (3pp).

\* cited by examiner

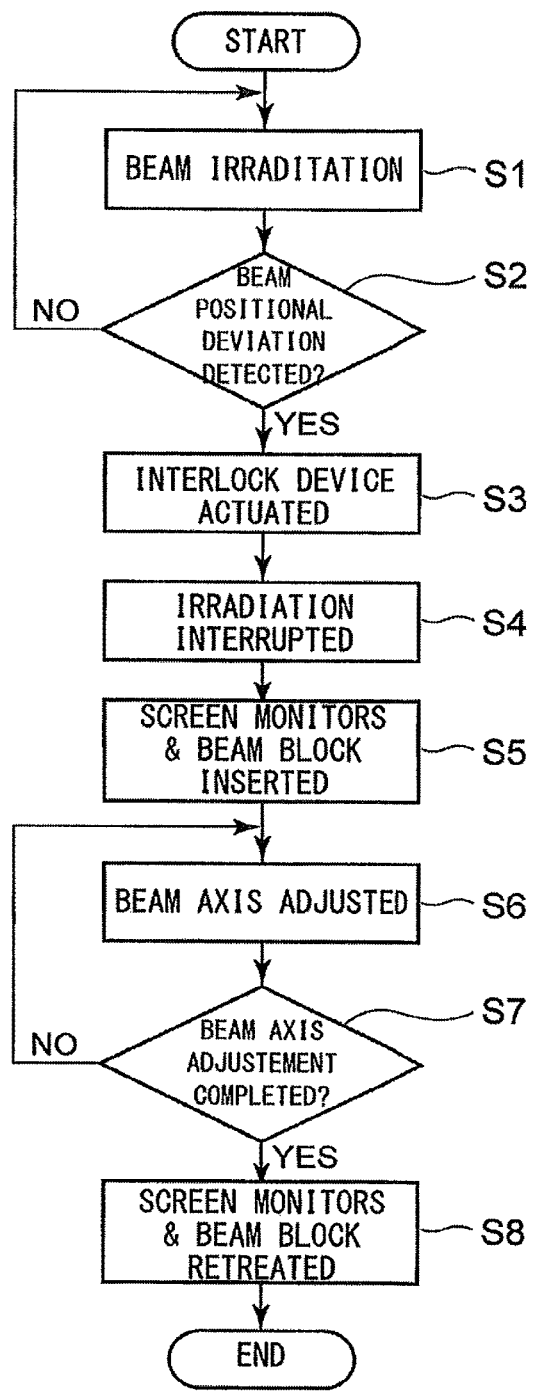

PARTICLE BEAM ADJUSTMENT DEVICE, PARTICLE BEAM ADJUSTMENT METHOD, AND PARTICLE BEAM THERAPEUTIC DEVICE

TECHNICAL FIELD

The embodiment of the present invention relates to a particle beam adjustment device and adjustment method that control the trajectory of a particle beam such as a carbon beam or proton beam with respect to an irradiation target and a particle beam therapeutic device using the particle beam adjustment device.

BACKGROUND ART

In general, a particle beam therapeutic device is used to irradiate the affected part of a cancer patient with a particle beam (hereinafter referred to merely as "beam") such as a carbon beam or proton beam. A particle beam irradiation method currently used includes an expanded beam method. In the expanded beam method, a beam diameter of the particle beam is expanded to a size equal to or larger than the size of the affected part of a cancer patient. However, the expanded beam method cannot strictly three-dimensionally match the beam with the shape of the affected part, and there is a limit in reducing influence on normal tissues around the affected part.

Then, as a further advanced irradiation method of particle beam therapy, a scanning irradiation method is now being put into practice. This method virtually divides the affected part of a patient into a three-dimensional lattice points and performs irradiation to each lattice point. This scanning irradiation method includes, for example, a three-dimensional irradiation method called "spot scanning irradiation method". In the spot scanning irradiation method, each spot (point) is irradiated in the following way.

When a predetermined dose of radiation has been applied to a certain spot in an affected part under the control of a beam emission control device, the scanning control device outputs a spot switching command signal upon receiving a radiation dosage termination signal from a dose monitor. Based on the spot switching command signal, the beam emission control device stops beam emission.

At the same time, an electromagnet power supply for supplying an exciting current to an irradiation field forming electromagnet to scan the particle beam starts setting a current value corresponding to the coordinates of the next irradiation spot. The scanning control device, upon receiving a setting completion signal for the set current value of the electromagnet power supply, outputs a beam irradiation start command signal to the beam emission control device, and the irradiation to the next point is started. This is sequentially repeated to irradiate a treatment area with respect to one irradiation slice.

When the irradiation for one irradiation slice is completed, the beam emission is temporarily interrupted. Then, the beam termination position (slice) in the beam travelling direction changed by changing energy of the beam emitted from an accelerator or by controlling a range adjustment apparatus called a range shifter. In this way, the scanning irradiation and the slice switching are sequentially performed for irradiation over the entire treatment area.

In the above scanning irradiation method, a position monitor is provided at an irradiation port to allow the operator to check if the beam is being irradiated to a correct position. If there occurs a current setting abnormality of the electromagnet power supply for supplying an exciting current to the irradiation field forming electromagnet, or trajectory deviation of beam in the beam transport direction from an upstream-side accelerator to a downstream side scanning irradiator, a difference occurs between an irradiation trajectory pre-determined and an irradiation trajectory measured by the position monitor. In this case, an interlock signal (emergency stop signal) is output from a position monitor controller provided in the scanning control device to interrupt therapeutic irradiation.

Possible causes for the beam trajectory deviation include, for example, a change in the magnetic field of an electromagnet in a path for transporting the beam from an accelerator to a treatment room. When such a magnetic field change occurs, the beam is not transported on a correct trajectory, making it impossible to ensure quality sufficient as the therapeutic beam.

To operate a particle beam therapeutic device that employs the scanning irradiation method, every morning an operator corrects setting values set in an operation unit for operating the beam for each irradiation beam set energy while checking beam trajectory to thereby check the quality of the beam used for scheduled therapy.

Specifically, a pair of screen monitors each forming a fluorescent film are disposed on the beam trajectory so as to be spaced apart from each other at a predetermined distance. The operator adjusts the current values of correcting electromagnets based on a deviation amount (deviation amount from an ideal center trajectory free from beam trajectory deviation) calculated from output values from these screen monitors, thereby correcting the beam trajectory.

Further, even when the setting value set in the operation unit for operating the beam remains unchanged, it may not be always true, because of a temperature change or the like, that a deviation amount of the beam trajectory during the morning and that during the afternoon are the same. Thus, when a beam position abnormality is detected by the position monitor at the irradiation start or during irradiation, the therapeutic irradiation may not be accomplished.

In the technique described in Patent Document 1, there are provided a first beam position monitor that detects a beam passing position on the irradiation nozzle upstream side and a second beam position monitor that detects a beam passing position on the irradiation nozzle downstream side.

CITATION LIST

Patent Document

Patent Document 1: JP 2003-282300A

SUMMARY OF THE INVENTION

Problems to be Solved by the Invention

In the above-mentioned particle beam therapeutic device using the scanning irradiation method, the pair of screen monitors are disposed outside the treatment room, and the beam trajectory is corrected by a trajectory distanced from the trajectory with respect to a patient, so that the distance between the downstream-side screen monitor and the patient is larger than the distance between the pair of screen monitors. This limits beam trajectory accuracy to be obtained. As a result, when a beam trajectory further deviates because of a change in environmental factors such as temperature, the therapeutic irradiation is highly likely to be interrupted in response to detection of the deviation by the position monitor.

Further, when the position monitor detects a beam positional deviation during therapeutic irradiation, it is necessary to correct the beam trajectory during the irradiation interruption. For the purpose of making the correction without prompting the patient to leave the beam irradiation position, a beam block is installed at a beam inlet in the treatment room. The beam block has a size so large that can block the beam inlet.

The pair of screen monitors are disposed upstream of the thus provided beam block in the beam transport direction. In this case, the screen monitors cannot accurately catch a beam axis deviation unless they are disposed spaced apart from each other at a predetermine distance.

The pair of screen monitors, if disposed upstream of the large beam block in the beam transport direction as described above, require a large space for installation, and because of the constraints on the size of the entire device, a predetermined distance may not be ensured between the pair of screen monitors. This hampers the screen monitors from accurately detecting the beam axis deviation, which does not allow for highly accurate adjustment of beam axis deviation.

The object of the present embodiment is to provide a particle beam adjustment device and adjustment method, and a particle beam therapeutic device capable of improving accuracy of the beam trajectory.

Means for Solving the Problem

In order to achieve the object, there is presented an embodiment of a particle beam adjustment device comprising: a position monitor that detects a positional deviation of a particle beam transported from a beam transport section; an interlock device to interrupt irradiation of the particle beam when a positional deviation of the particle beam is detected by the position monitor; a pair of screen monitors that measure position and angle of an axis of the particle beam; a correction electromagnet that controls the axis of the particle beam by adjusting a magnetic field on a basis of a signal indicating the particle beam position and angle measured by the screen monitors; and a beam scanning electromagnet that irradiates an irradiation target with the particle beam, wherein one of the pair of screen monitors is installed outside a treatment room, and the other one of the pair of screen monitors and the position monitor are installed inside the treatment room.

There is also presented a particle beam adjustment device comprising: a position monitor that detects a positional deviation of a particle beam transported from a beam transport section; an interlock device to interrupt irradiation of the particle beam when a positional deviation of the particle beam is detected by the position monitor; a beam scanning electromagnet that irradiates an irradiation target with the particle beam; and a beam block that shields the particle beam so as not to allow the particle beam to reach the irradiation target in a treatment room during adjustment of the axis of the particle beam, wherein the beam block and the position monitor are installed in the treatment room.

There is also presented a particle beam adjustment method comprising: a beam deviation detection step of detecting a deviation of an axis of a particle beam transported from a beam transport section, with a position monitor installed inside a treatment room; a measurement step of measuring position and angle of the axis of the particle beam using a screen monitor installed outside a treatment room and another screen monitor installed inside the treatment room; and a beam axis adjustment step of adjusting the axis of the particle beam by adjusting a magnetic field based on the position and angle of the axis of the particle beam measured in the measurement step.

There is also presented a particle beam irradiation device comprising: a beam generation section that generates a particle beam; a beam emission controller that controls emission of the particle beam; a beam transport section that transports the particle beam to an irradiation target in a treatment room; a position monitor that detects a positional deviation of the particle beam transported from the beam transport section: an interlock device to interrupt irradiation of the particle beam when a positional deviation of the particle beam is detected by the position monitor; a pair of screen monitors that measure position and angle of an axis of the particle beam; a correction electromagnet that controls the axis of the particle beam by adjusting a magnetic field on the basis of a signal indicating the particle beam position and angle measured by the screen monitors; and a beam scanning electromagnet that irradiates an irradiation target with the particle beam, wherein one of the pair of screen monitors is installed outside the treatment room, and the other one of the pair of screen monitors and the position monitor are installed inside the treatment room.

Advantage of the Invention

According to the present embodiment, the accuracy of the beam trajectory can be improved.

BRIEF DESCRIPTION OF THE DRAWINGS

FIG. 5 is a flowchart illustrating a procedure for correcting the beam trajectory in the embodiment.

EMBODIMENT CARRYING OUT THE INVENTION

Hereinafter, a beam adjustment device as an accelerator according to an embodiment of the present invention and a particle beam therapeutic device using the beam adjustment device will be described with reference to the accompanying drawings.

Figure 1:
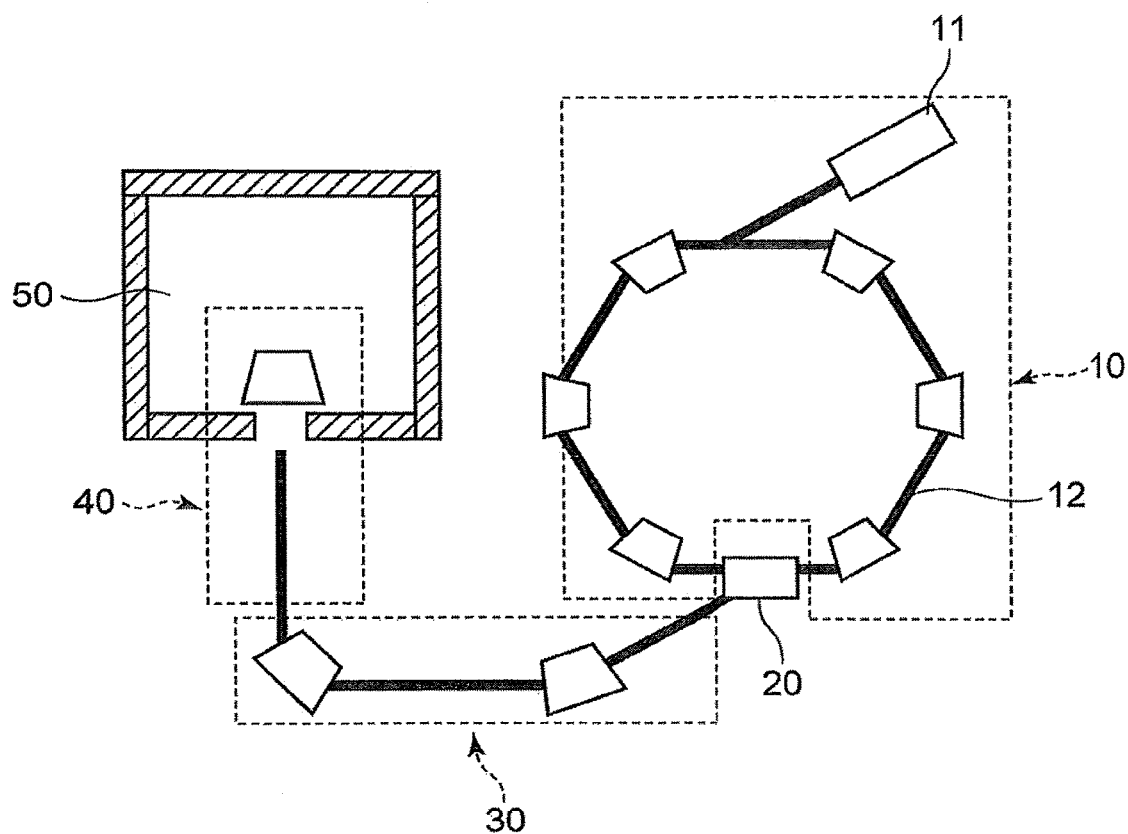
FIG. 1 is a schematic plan view illustrating an entire configuration of a particle beam therapeutic device to which the present embodiment is applied.
Figure 2:
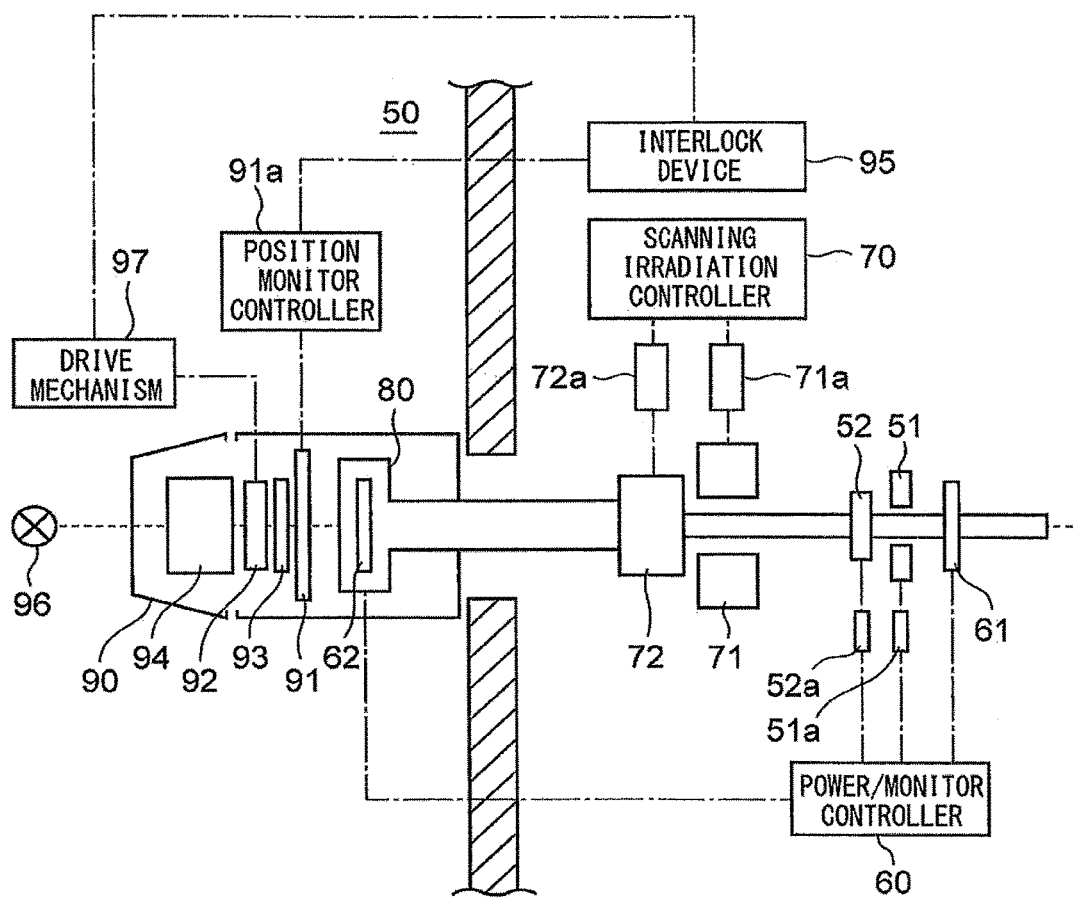
FIG. 2 is a block diagram illustrating the configurations of an irradiation device section of FIG. 1 and its related devices.

FIG. 1 is a schematic plan view illustrating an entire configuration of a particle beam therapeutic device to which the present embodiment is applied. FIG. 2 is a block diagram illustrating the configurations of an irradiation device section of FIG. 1 and its related devices.

As illustrated in FIG. 1, the particle beam therapeutic device according to the present embodiment includes a beam generation section 10, a beam emission control section 20, a beam transport section 30, an irradiation device section 40 having main constituent components of the present embodiment, and a treatment room 50. The beam generation section 10 has an unillustrated ion source, a beam incident system 11, and a circular accelerator 12.

As illustrated in FIG. 2, the irradiation device section 40 has a horizontal correction electromagnet 51, a horizontal correction electromagnet power supply 51a, a vertical correction electromagnet 52, a vertical correction electromagnet power supply 52a, a screen monitor 61, a power/monitor controller 60, a horizontal irradiation field forming electromagnet 71 as a beam scanning electromagnet, a horizontal irradiation field forming electromagnet power supply 71a, a vertical irradiation field forming electromagnet 72 as a beam scanning electromagnet, a vertical irradiation field forming electromagnet power supply 72a, a scanning irradiation controller 70, and an interlock device 95.

The irradiation device section 40 has an irradiation port 90 provided in the treatment room 50. A vacuum duct 80 is provided in the irradiation port 90. A screen monitor 62 is provided in the vacuum duct 80.

In the irradiation port 90, a position monitor 91, a beam block 92, a ridge filter 93, and a range shifter 94 are provided. The position monitor 91 is electrically connected to the interlock device 95 through a position monitor controller 91a.

The screen monitors 61 and 62 make a pair. The screen monitors 61 and 62 are inserted into a beam line only when a beam axis is adjusted, and retreat from the beam line during therapeutic irradiation. Therefore, the screen monitors 61 and 62 are configured to advance and retreat with respect to the beam line by an unillustrated drive mechanism.

The screen monitors 61 and 62 are provided for measuring a beam position during beam axis adjustment. By pairing the screen monitors 61 and 62, a beam trajectory (beam position and beam angle) can be computed. A signal indicating the beam position and beam angle measured by the screen monitors 61 and 62 is output to the power/monitor controller 60.

The horizontal correction electromagnet 51 and the vertical correction electromagnet 52 are electromagnets for adjusting a magnetic field on the basis of the signal indicating the beam position and the beam angle measured by the screen monitors 61 and 62 to align a beam axis with an irradiation coordinate reference point (hereinafter, referred to as "isocenter") 96 of an affected part of a patient as an irradiation target. The horizontal correction electromagnet 51 and the vertical correction electromagnet 52 adjust current values of the horizontal correction electromagnet power supply 51a and the vertical correction electromagnet power supply 52a corresponding to the respective horizontal correction electromagnet 51 and the vertical correction electromagnet 52 to change a magnetic field.

The irradiation field forming electromagnets are constituted of the pair of horizontal irradiation field forming electromagnet 71 and the vertical irradiation field forming electromagnet 72, and the horizontal irradiation field forming electromagnet 71 and the vertical irradiation field forming electromagnet 72 are disposed between the screen monitors 61 and 62. The horizontal irradiation field forming electromagnet 71 and the vertical irradiation field forming electromagnet 72 are electromagnets for two-dimensionally scanning the affected part with a beam along the profile of the affected part. The horizontal irradiation field forming electromagnet 71 and the vertical irradiation field forming electromagnet 72 receive power supply from the horizontal irradiation field forming electromagnet power supply 71a and the vertical irradiation field forming electromagnet power supply 72a, respectively.

The position monitor 91 detects the beam position scanned during therapeutic irradiation and monitors whether or not there is a significant deviation from a preset position. When detecting a significant deviation, the position monitor 91 outputs an interlock signal to the interlock device 95 through the position monitor controller 91a.

The ridge filter 93 adjusts a beam distribution in the depth direction in accordance with an interval between irradiation slices. The ridge filter 93 is configured by arranging substantially triangular shaped bar-like members made of metal such as aluminum in the lateral direction.

The range shifter 94 is adapted to change beam energy, i.e., the depth of a beam stop position in the body. The range shifter 94 is formed of a material such as acrylic and constituted of a plurality of plates different in thickness. By changing a combination of the plurality of plates different in thickness, the beam stop point can be varied.

The beam block 92 is configured to advance and retreat with respect to the beam line by a drive mechanism 97, like the screen monitors 61 and 62 driven by an unillustrated drive mechanism. The beam block 92 is inserted into the beam line during adjustment of the beam axis to stop the beam to thereby prevent the beam from reaching the isocenter 96. When the beam position is detected by the position monitor 91, and a significant deviation is found, an interlock signal is output to the interlock device 95. Then, the interlock device 95 outputs an operation signal to the drive mechanism 97. When the drive mechanism 97 operates, the beam block 92 is inserted into the beam line. On the other hand, during therapeutic irradiation, the drive mechanism 97 operates to make the beam block 92 retreat from the beam line.

The following describes the operation of the accelerator according to the present embodiment.

The ion source in the beam generation section 10 generates a beam. The beam incident system 11 accelerates the generated beam to a possible energy level. The accelerated beam enters the circular accelerator 12.

Once the beam enters the circular accelerator 12, it repeats to enter the circular accelerator 12 a prescribed number of times while orbiting therearound. After completion of the orbiting/entering, the beam is further accelerated to an energy level required for cancer treatment.

After the beam acceleration, the accelerated beam is taken out in an emission trajectory by the beam emission control section 20 and transported to the irradiation device section 40 by way of the beam transport section 30. The irradiation device section 40 irradiates the isocenter 96 as an irradiation target with the beam for cancer treatment.

The following describes the operation of beam axis adjustment according to the present embodiment.

An unillustrated drive mechanism is operated to insert the screen monitors 61 and 62 into the beam line. At the same time, the drive mechanism 97 is operated to insert the beam block 92 into the beam line. Further, the pair of horizontal irradiation field forming electromagnet 71 and the vertical irradiation field forming electromagnet 72 are supplied with current from the horizontal irradiation field forming electromagnet power supply 71a and the vertical irradiation field forming electromagnet power supply 72a, respectively, in a current pattern for demagnetization. As a result, the magnetic fields of the horizontal irradiation field forming electromagnet 71 and the vertical irradiation field forming electromagnet 72 become substantially zero. In this state, the beam is introduced into the irradiation device section 40, and the screen monitors 61 and 62 detect the beam axis positions. This will be described more in detail with reference to FIGS. 3 and 4.

Figure 3:
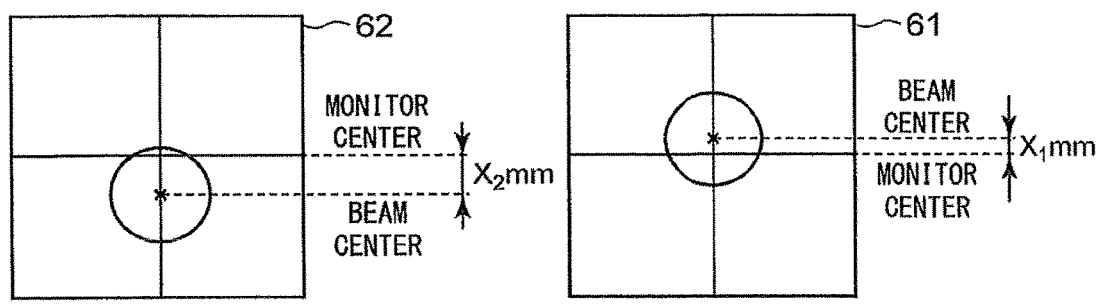
FIG. 3 is an explanatory view illustrating the pair of screen monitors in the embodiment.
Figure 4:
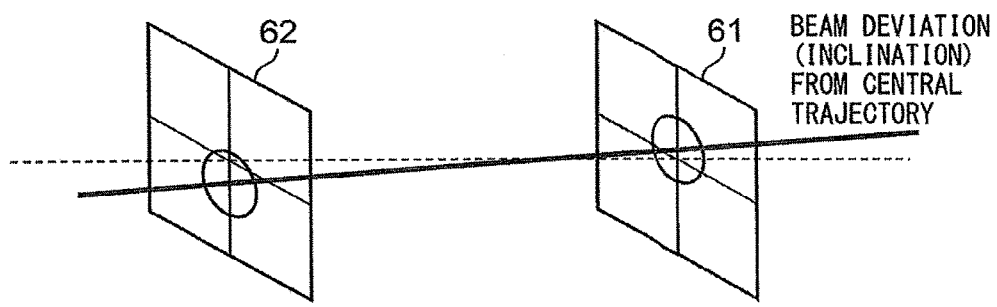
FIG. 4 is an explanatory view illustrating a beam trajectory adjustment method using the screen monitors of FIG. 3.

FIG. 3 is an explanatory view illustrating the pair of screen monitors in the embodiment. FIG. 4 is an explanatory view illustrating a beam trajectory adjustment method using the screen monitors of FIG. 3.

As illustrated in FIG. 3, beam profiles on fluorescent films of the respective screen monitors 61 and 62 are observed through an unillustrated CCD camera, and the resultant images are analyzed to calculate deviation amounts X1 and X2 between the beam center and the monitor center.

When the deviation amounts $X_1$ and/or $X_2$ exceed a preset threshold value, current correction amounts of the horizontal correction electromagnet power supply 51a and/or the vertical correction electromagnet power supply 52a are calculated from the deviation amounts $X_1$ and/or $X_2$ by the power/monitor controller 60, and signals corresponding to the corrected current values are output to the horizontal correction electromagnet power supply 51a and the vertical correction electromagnet power supply 52a. The above threshold value is a therapeutically acceptable deviation amount of the beam axis.

Thus, by changing the magnetic fields of the horizontal correction electromagnet 51 and the vertical correction electromagnet 52, the beam axis can be aligned with the isocenter 96.

In the meantime, existence of the resolution of the above CCD camera and alignment error (deviation from a set position) of the screen monitors 61 and 62 disposed on the beam line limits adjustment accuracy of the beam trajectory using the screen monitors 61 and 62.

Therefore, bringing the screen monitor 62 close to an affected part of patient's body in the present embodiment leads to improvement in beam trajectory accuracy that can be regarded as the performance of the particle beam therapeutic device. Specifically, in the present embodiment, the screen monitor 62 of downstream side, in the beam transport direction, is disposed in the treatment room 50, whereby a sufficient distance can be ensured between the two screen monitors 61 and 62. In addition, the downstream-side screen monitor 62 can be positioned close to the isocenter 96.

As described above, in the present embodiment, it is possible to ensure a sufficient distance between the two screen monitors 61 and 62, making it possible to accurately grasp the beam axis deviation, which in turn can improve the beam trajectory accuracy.

Further, it is possible to position the downstream-side screen monitor 62 close to the isocenter 96, whereby the beam trajectory accuracy with respect to the isocenter 96 can be further improved.

Further, by accommodating the screen monitors 61 and 62 in the vacuum duct 80, a vacuum region can be made close to the vicinity of the isocenter 96 as much as possible, so that the beam is not transported in the atmosphere over a long distance, suppressing scattering of the beam. As a result, an affected part can be irradiated with a thin beam during therapeutic irradiation.

Further, during beam axis adjustment, in order to suppress beam leakage to a downstream-side affected part in the beam transport direction, the beam block 92 is provided in the irradiation port 90. As a result, when the beam trajectory is to be corrected, the beam block 92 is inserted into the beam line to shield the beam. (During therapeutic irradiation, the beam block 92 is put off the beam trajectory.)

The beam block 92 is designed to have an optimum thickness that shields the beam emitted during the beam trajectory adjustment and does not have influence of radiation exposure on the downstream affected part in the beam transport direction. Thus, even if the position monitor 91 detects a positional deviation of the beam during therapeutic irradiation, it is possible to correct the beam trajectory in the following procedure without prompting the patient to move off the beam irradiation position during interruption of the therapeutic irradiation.

FIG. 5 is a flowchart illustrating a procedure for correcting the beam trajectory in the embodiment.

A patient is placed on a treatment table set in the treatment room 50 and positioned in advance.

First, beam irradiation is started (step S1). Then, in step S2, the beam irradiation is continued until the position monitor 91 detects a positional deviation of the beam. When the beam positional deviation is detected (YES in step S2), the processing advances to step S3, where the interlock device 95 is actuated. Then, the interlock device 95 outputs an interlock signal to interrupt the beam irradiation (step S4).

Subsequently, an unillustrated drive mechanism is operated to insert the screen monitors 61 and 62 into the beam line, and the drive mechanism 97 is operated to insert the beam block 92 in the beam line (step S5).

Further, in step S6, the beam axis is adjusted. In the beam axis adjustment, the beam is introduced to the irradiation device section 40 in a state as described above, and the screen monitors 61 and 62 are used to detect beam axis positions. Signals indicating the beam deviation amounts detected by the screen monitors 61 and 62 are output to the power/monitor controller 60. The power/monitor controller 60 calculates current correction amounts of the horizontal correction electromagnet power supply 51a and the vertical correction electromagnet power supply 52a. Then, the power/monitor controller 60 outputs signals corresponding to the corrected current values to the horizontal correction electromagnet power supply 51a and the vertical correction electromagnet power supply 52a and sets them therein. With this correction and setting, the horizontal correction electromagnet 51 and the vertical correction electromagnet 52 change their magnetic fields to adjust the beam axis.

Then, when the beam axis adjustment is completed (YES in step S7), the processing flow advances to step S8. In step S8, the unillustrated drive mechanism is operated again to make the screen monitors 61 and 62 retreat from the beam line, and the drive mechanism 97 is operated to make the beam block 92 retreat from the beam line. Then, the beam trajectory correction operation is completed, and beam irradiation is resumed.

When the beam irradiation is stopped in the middle of the irradiation, a residual magnetic field may remain in the horizontal irradiation field forming electromagnet 71 and/or the vertical irradiation field forming electromagnet 72. Therefore, a step of demagnetizing the horizontal irradiation field forming electromagnet 71 and the vertical irradiation field forming electromagnet 72 is preferably inserted between steps S5 and S6. For example, a current pattern defined for demagnetization is supplied to the horizontal irradiation field forming electromagnet 71 from the horizontal irradiation field forming electromagnet power supply 71a and the vertical irradiation field forming electromagnet 72 from the vertical irradiation field forming electromagnet power supply 72a.

In conventional general particle beam therapeutic devices, a patient needs to get off once from the treatment bed so as to avoid his or her exposure to radiation. However, in the present embodiment, the beam is shielded with the beam block 92, and thus patient's exposure to radiation can be avoided, thereby eliminating the need for the patient to get off from the treatment bed. Thus, beam irradiation for cancer treatment can be resumed in a short time, thereby significantly reducing physical burden on the patient.

Further, in the present embodiment, the beam block 92 is disposed downstream of the position monitor 91 so as to allow the position monitor 91 to monitor the beam even when the beam is being shielded. Thus, the beam trajectory can be checked (cross-checked) on both the position monitor 91 and the downstream-side screen monitor 62. This can increase reliability of the beam position.

Further, in the present embodiment, the range shifter 94 is disposed downstream of the beam block 92, and the range shifter 94 is fully inserted into the beam line while the beam is being shielded, whereby beam shielding effect can be further enhanced.

Further, in the present embodiment, the screen monitor 62 disposed in the treatment room 50 is accommodated in the vacuum duct 80, whereby it is possible to bring a vacuum region close to the immediately upstream of the position monitor 91, thereby reducing influence of scattering of the particle beam, which enables a sufficient beam quality to be ensured.

As described above, in the spot scanning irradiation method, improvement in the performance of the beam itself is directly reflected in therapeutic efficacy. Thus, according to the present embodiment, the beam trajectory adjustment accuracy, operability between interruption and resuming of the beam irradiation, and the quality of the therapeutic beam can be improved.

Other Embodiments

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, in the above described embodiment, if the position monitor 90 has detected a beam deviation during therapeutic irradiation, the beam block 92 is inserted into the beam line in order to adjust the beam trajectory without the patient's evacuation from the irradiation position. Alternatively, the beam block 92 may be omitted if the patient evacuates from the irradiation position.

EXPLANATION OF SYMBOLS

10: beam generation section; 11: beam incident system; 12: circular accelerator; 20: beam emission control section; 30: beam transport section; 40: irradiation device section; 50: treatment room; 51: horizontal correction electromagnet; 51a: horizontal correction electromagnet power supply; 52: vertical correction electromagnet; 52a: vertical correction electromagnet power supply; 60: power/monitor controller; 61: screen monitor; 62: screen monitor; 70: scanning irradiation controller; 71: horizontal irradiation field forming electromagnet (beam scanning electromagnet); 71a: horizontal irradiation field forming electromagnet power supply; 72: vertical irradiation field forming electromagnet (beam scanning electromagnet); 72a: vertical irradiation field forming electromagnet power supply; 80: vacuum duct; 90: irradiation port; 91: position monitor; 91a: position monitor controller; 92: beam block; 93: ridge filter; 94: range shifter; 95: interlock device; 96: isocenter (irradiation target); 97: drive mechanism

What is claimed is:

1. A particle beam adjustment device comprising:
a position monitor that detects a positional deviation of a particle beam transported from a beam transport section;
an interlock device to interrupt irradiation of the particle beam when a positional deviation of the particle beam is detected by the position monitor;
a pair of screen monitors that measure position and angle of an axis of the particle beam;
a correction electromagnet that controls the axis of the particle beam by adjusting a magnetic field on a basis of a signal indicating the particle beam position and angle measured by the screen monitors; and
a beam scanning electromagnet that irradiates an irradiation target with the particle beam, and
a beam block that shields the particle beam so as not to allow the particle beam to reach the irradiation target in the treatment room during adjustment of the axis of the particle beam, wherein
one of the pair of screen monitors is installed outside a treatment room, and the other one of the pair of screen monitors and the position monitor are installed inside the treatment room,
the beam block is configured to advance and retreat with respect to a beam line along which the particle beam is transported, and
the position monitor is installed upstream of the beam block in a transport direction of the particle beam.

2. The particle beam adjustment device according to claim 1, wherein a range shifter that changes a stop point of the particle beam is installed downstream of the beam block in the particle beam transport direction.

3. The particle beam adjustment device according to claim 1, wherein the pair of screen monitors are accommodated in a vacuum duct.

4. The particle beam adjustment device according to claim 1, wherein the pair of screen monitors are configured to advance and retreat with respect to a beam line along which the particle beam is transported.

5. A particle beam adjustment device comprising:
a position monitor that detects a positional deviation of a particle beam transported from a beam transport section;
an interlock device to interrupt irradiation of the particle beam when a positional deviation of the particle beam is detected by the position monitor;
a beam scanning electromagnet that irradiates an irradiation target with the particle beam; and
a beam block that shields the particle beam so as not to allow the particle beam to reach the irradiation target in a treatment room during adjustment of the axis of the particle beam, wherein
the beam block and the position monitor are installed in the treatment room,
the beam block is configured to advance and retreat with respect to a beam line along which the particle beam is transported, and
the position monitor is installed upstream of the beam block in a transport direction of the particle beam.

6. The particle beam adjustment device according to claim 5, wherein a range shifter that changes a stop point of the particle beam is installed downstream of the beam block in the particle beam transport direction.

7. A particle beam irradiation device comprising:
a beam generation section that generates a particle beam;
a beam emission controller that controls emission of the particle beam;
a beam transport section that transports the particle beam to an irradiation target in a treatment room;
a position monitor that detects a positional deviation of the particle beam transported from the beam transport section;
an interlock device to interrupt irradiation of the particle beam when a positional deviation of the particle beam is detected by the position monitor;
a pair of screen monitors that measure position and angle of an axis of the particle beam;
a correction electromagnet that controls the axis of the particle beam by adjusting a magnetic field on the basis of a signal indicating the particle beam position and angle measured by the screen monitors; and
a beam scanning electromagnet that irradiates an irradiation target with the particle beam, and
a beam block that shields the particle beam so as not to allow the particle beam to reach the irradiation target in the treatment room during adjustment of the axis of the particle beam, wherein
one of the pair of screen monitors is installed outside the treatment room, and the other one of the pair of screen monitors and the position monitor are installed inside the treatment room,
the beam block is configured to advance and retreat with respect to a beam line along which the particle beam is transported, and
the position monitor is installed upstream of the beam block in a transport direction of the particle beam.

* * * * *